United States Patent [19]

Knifton et al.

[11] Patent Number: 5,364,981
[45] Date of Patent: Nov. 15, 1994

[54] ON-STEP SYNTHESIS OF METHYL T-BUTYL ETHER FROM T-BUTANOL USING PLATINUM/PALLADIUM MODIFIED β-ZEOLITE CATALYSTS

[75] Inventors: John F. Knifton, Austin; Pei-Shing E. Dai, Port Arthur, both of Tex.

[73] Assignee: Texaco Chemical Company, White Plains, N.Y.

[21] Appl. No.: 148,248

[22] Filed: Nov. 8, 1993

[51] Int. Cl.$^5$ ............................................. C07C 41/09
[52] U.S. Cl. .................................................. 568/698
[58] Field of Search ....................................... 568/698

[56] References Cited

U.S. PATENT DOCUMENTS

| | | | |
|---|---|---|---|
| 4,886,918 | 12/1989 | Sorensen et al. | 568/617 |
| 5,081,318 | 1/1992 | Knifton | 568/698 |
| 5,102,428 | 4/1992 | Owen et al. | 568/698 |

*Primary Examiner*—Howard T. Mars
*Attorney, Agent, or Firm*—James L. Bailey; Kenneth R. Priem; Cynthia L. Kendrick

[57] ABSTRACT

Disclosed is an improved process for preparing alkyl tertiary alkyl ethers, especially methyl t-butyl ether, in one step which comprises reacting tertiary butanol and methanol in the presence of a catalyst comprising β-zeolite modified with one or more metals selected from Group VIII of the Periodic Table, and optionally further modified with a halogen or a Group IB metal, with an alumina binder, at a temperature of about 20° C. to 250° C. and atmospheric pressure to about 1000 psig, wherein when the temperature is in the operating range above about 140° C., the product comprises a two-phase mix of an MTBE-isobutylene and, optionally, diisobutylene product-rich phase and a heavier aqueous ethanol-rich phase.

21 Claims, No Drawings

ON-STEP SYNTHESIS OF METHYL T-BUTYL ETHER FROM T-BUTANOL USING PLATINUM/PALLADIUM MODIFIED β-ZEOLITE CATALYSTS

CROSS-REFERENCE

This application is related to pending U.S. Ser. Nos. 08/096,873 and 08/057,373. It is also related to U.S. Pat. Nos. 4,822,921; 4,827,048; 5,099,072; 5,081,318; 5,059,725; 5,157,162; 5,162,592; 5,157,161; 5,183,947; and allowed U.S. Ser. Nos. 07/917,218; 07/878,121; and 07/917,885, all of which are incorporated by reference herein in their entirety.

FIELD OF THE INVENTION

This invention concerns an improved process for preparing alkyl tertiary alkyl ethers and particularly methyl tertiary butyl ether (MTBE) in one step by the reaction of tertiary butanol and methanol in the presence of a catalyst comprising a Beta (β) zeolite modified with one or more metals selected from Group VIII of the Periodic Table, as defined in the Condensed Chemical Dictionary, page 789. Particularly good etherification activity has been observed using platinum or palladium. The novel catalysts may optionally be further treated with a halogen or a Group IB metal. The invention is especially advantageous in that the platinum/palladium-modified zeolites exhibit both high activity during methyl t-butyl ether synthesis from methanol plus t-butanol, as well as ethyl t-butyl ether synthesis from ethanol plus t-butanol and, additionally, allow for the cosynthesis of isobutylene and diisobutylene.

BACKGROUND OF THE INVENTION

It is well-known that there is pressure to eliminate lead compounds from fuels for reasons of public health and environmental protection. Although the specifications for reformulated gasolines set by EPA will come into force in 1995, standards were brought into force on November 1, 1992 requiring gasoline contain 2.7 wt % oxygen during the winter in nonattainment areas of the U.S. If the federal air quality standard for CO has not been achieved by a specified attainment date, the minimum oxygen content will increase to 3.1%. Moreover, starting in the summer of 1992, the maximum blending Reid vapor pressure (BRvp) of all gasolines is set at 9.0 psi. Since oxygenates are not only used as gasoline blending components, extenders, octane boosters and as key ingredients for reducing the emissions of CO and VOCs (Volatile Organic Compounds), it is expected that the demand for oxygenates will increase enormously in the coming years. See F. Cunill, et al., "Effect of Water Presence on Methyl tert-Butyl Ether and Ethyl tert-Butyl Ether Liquid-Phase Synthesis". IND. ENG. CHEM. RES. 1993, 32, 564–569.

Of all oxygenates, the tertiary ethers, such as methyl t-butyl ether (MTBE), ethyl tert-butyl ether (ETBE), and tert-amyl methyl ether (TAME) are preferred by refineries to lighter alcohols. They have lower blending Ried vapor pressure (BRvp), lower vaporization latent heats and low solubilities in water. The most common ether in use today is MTBE with a production of about 25 million metric tons. However, ETBE is becoming more attractive as the price of methanol goes up in relation to gasoline. It can be produced from renewable ethanol, in contrast to methanol derived from natural gas, and its use would help mitigate the greenhouse effect, Ibid., p. 564.

In addition, ETBE outranks MTBE as an octane enhancer and its BRvp is only 4 psi, which makes it more attractive for BRvp blends less than 8 psi required in some places during the summer. Therefore, a number of U.S. states and European countries are planning to make ETBE from bioethanol, Ibid.

At the present time, TAME, which is usually produced in MTBE refinery units when $C_5$ olefins are diverted into the feed, is not viewed as rivaling MTBE or ETBE, Ibid.

In an article entitled "$C_5$ Olefins—The New Refinery Challenge," Kerry Rock et al. discuss the removal of FCC $C_5$ olefins. See FUEL REFORMULATION, Vol. 2, No. 6, p. 42.

The main drawback of tertiary ethers, is that they substantially increase aldehyde emissions which are under EPA regulations and have to decrease 15% by 1995. It is believed this drawback could be largely circumvented by mixing the tertiary ethers with tertiary alcohols. Tertiary butyl alcohol (tBA) has a very low atmospheric reactivity and low aldehyde emissions, since no hydrogens are contained in the carbon link to the oxygen. Basis experience acquired with tBA during the 1970s, a gasoline blended with a mixture of ethers and tBA and/or tertiary amyl alcohol should be shippable, Ibid.

Generally, it is known that asymmetrical $C_4$–$C_7$ alkyl tertiary alkyl ethers are particularly useful as octane improvers for liquid fuels, especially gasoline. Methyl tertiary butyl ether (MTBE), ethyl t-butyl ether (ETBE), isopropyl t-butyl ether (IPTBE) and tertiary amyl methyl ether (TAME) are known to exhibit high octane properties. Much attention has been focused on production of these ethers due to the rapidly increasing demand for lead-free octane boosters for gasoline.

It is known in the art to produce MTBE or ETBE by reacting isobutylene with either methanol or ethanol, resulting in the formation of MTBE or ETBE, respectively. The reaction normally is conducted in liquid phase with relatively mild conditions. The isobutylene can be obtained from various sources, such as naphtha cracking, catalytic cracking, etc. The resulting reaction product stream contains the desired MTBE or ETBE, as well as unreacted isobutene and other $C_4$ hydrocarbons and methanol or ethanol.

A number of U.S. patents and allowed U.S. applications assigned to Texaco Chemical Co. disclose methods of making alkyl tertiary alkyl ethers in one step.

In U.S. Pat. No. 4,822,921, to Texaco Chemical Co., there is described a method for preparing alkyl tertiary alkyl ethers which comprises reacting a $C_1$–$C_6$ primary alcohol with a $C_4$–$C_{10}$ tertiary alcohol over a catalyst comprising an inert support impregnated with phosphoric acid.

U.S. Pat. No. 4,827,048, to Texaco Chemical Co., describes a method for preparing alkyl tertiary alkyl ethers from the same reactants using a heteropoly acid on an inert support.

U.S. Pat. No. 5,099,072, to Texaco Chemical Co., discloses a method for preparing alkyl tertiary alkyl ethers over an acidic montmorillonite clay catalyst which possesses very specific physical parameters.

U.S. Pat. No. 5,081,318, to Texaco Chemical Co., discloses a method for preparing alkyl tertiary alkyl ethers by reacting a $C_1$–$C_6$ primary alcohol with a $C_4$–$C_{10}$ tertiary alcohol over a catalyst comprising a fluorosulfonic acid-modified zeolite.

U.S. Pat. No. 5,059,725, to Texaco Chemical Co., discloses a method for preparing alkyl tertiary alkyl ethers from $C_1$–$C_6$ primary alcohols and $C_4$–$C_{10}$ tertiary alcohols over a catalyst comprising ammonium sulfate or sulfuric acid on a Group IV oxide.

U.S. Pat. No. 5,157,162, to Texaco Chemical Co., discloses a fluorosulfonic acid-modified clay catalyst for the production of alkyl tertiary alkyl ethers from $C_1$–$C_6$ primary alcohols and $C_4$–$C_{10}$ tertiary alcohols.

In U.S. Pat. No. 5,162,592, to Texaco Chemical Co. there is described a method for producing alkyl tertiary alkyl ethers from $C_1$–$C_6$ primary alcohols and $C_4$–$C_{10}$ tertiary alcohols using a multimetal-modified zeolite catalyst.

A hydrogen fluoride-modified montmorillonite clay catalyst is employed in U.S. Pat. No. 5,157,161, to Texaco Chemical Co., to produce alkyl tertiary alkyl ethers, including ETBE.

In U.S. Pat. No. 5,183,947, to Texaco Chemical Co., fluorophosphoric acid-modified clays are employed as catalysts in a method to produce alkyl tertiary alkyl ethers.

In allowed U.S. Ser. No. 07/917,218, assigned to Texaco Chemical Co., there is disclosed the use of a super acid alumina or a faujasite-type zeolite to produce alkyl tertiary alkyl ethers.

Allowed U.S. Ser. No. 07/878,121, to Texaco Chemical Co., discloses the use of a haloacid-modified montmorillonite clay catalyst to convert $C_1$–$C_6$ primary alcohols and $C_4$–$C_{10}$ tertiary alcohols to alkyl tertiary alkyl ethers.

Fluorophosphoric acid-modified zeolites are employed in allowed U.S. Ser. No. 07/917,885, to Texaco Chemical Co., to produce alkyl tertiary alkyl ethers.

Other references in the art which use tertiary butanol as a reactant and disclose MTBE or ETBE as a product usually require two stages rather than one.

The use of zeolites for certain reactions is known in the art. Beta-zeolite was first synthesized at Mobil R and D labs and exhibited improved thermal and acid stability over previously synthesized zeolites.

J. B. Higgins, et al. of Mobil Research and Development published an article in ZEOLITES, 1988, Vol. 8, November, 446–452 titled "The Framework Topology of Zeolite Beta." In the article Higgins et al. disclose what is known about the framework topology of $\beta$-zeolite. The information was determined using a combination of model building, distance-least-square refinement and powder pattern simulation.

In an article titled "Cumene Disproportionation over Zeolite $\beta$ I. Comparison of Catalytic Performances and Reaction Mechanisms of Zeolites," APPLIED CATALYSIS, 77 (1991) 199–207, Tseng-Chang Tsai, Chin-Lan Ay and Ikai Wang disclose a study demonstrating that cumene disproportionation can be applied as a probe reaction for zeolite structure. It is revealed that $\beta$-zeolite would have application potential in the production of diisopropylbenzene for reasons of activity, selectivity and stability.

In a second part of the article by Tsai et al., "II. Stability Enhancement with Silica Deposition and Steam Pretreatment", Ibid, pp. 209–222, Tsai and Wang disclose their development of two methods to improve the stability of $\beta$-zeolite, silica deposition and steam pretreatment.

E. Bourgeat-Lami et al. have published an article discussing their study of the effects of calcination of as synthesized or ammonium-exchanged forms of $\beta$-zeolite. See "Stability of the Tetrahedral Aluminum Sites in Zeolite Beta," E. Bourgeat et al., CATALYSIS LETTERS, 1990, 5, p. 265. These researchers came to the conclusion that the tetrahedral aluminum sites disappearing upon calcination can be readily restored by a simple treatment in ammonium nitrate. The parent sample of $\beta$-zeolite with a Si/Al ratio of 16.9 was synthesized at 130° C. using tetraethylammonium hydroxide as template. The NMR spectrum indicated a dealumination corresponding to about 25%. When this material was treated with ammonium nitrate solution, washed and over dried at 70° C., the signal of octahedral aluminum was no longer detected while that at 53 ppm narrowed and increased to 95% of its original value.

Patents in the art which employ $\beta$-zeolite relate mainly to dewaxing, and cracking of hydrocarbon feedstock.

An article titled "Beta Zeolite as Catalyst or Catalyst Additive for the Production of Olefins During Cracking of Gas Oil," was written by L. Bonetto et al., 9th International Zeolite Conference, July 1992, FP 22. The authors note that with the greater demand for oxygenated compounds there is indication there might be increased demands for catalysts and conditions which maximize $C_3$, $C_4$ and $C_5$ olefins. They suggest that $\beta$-zeolite could be used alone or combined with Y-zeolite as a suitable zeolite component. Various catalysts were studied with respect to minimization of diffusional requirements and zeolite stability.

U.S. Pat. No. 4,419,220, to Mobil, discloses a process for dewaxing a hydrocarbon feedstock containing straight chain paraffins which comprises contacting the feedstock with a $\beta$-zeolite catalyst having a Si:Al ratio of at least 30:1 and a hydrogenation component under isomerization conditions.

Another European Application to Mobil, EPO 0 094 827, discloses simultaneous catalytic hydrocracking and hydrodewaxing of hydrocarbon oils with $\beta$-zeolite.

In European Patent Application 0 095 303, to Mobil, there is a disclosure of dewaxing distillate fuel oils by the use of $\beta$-zeolite catalysts which, preferably have a silica:alumina ratio over 100:1. Ratios as high as 250:1 and 500:1 are disclosed as useful.

Another U.S. Pat. 4,518,485, to Mobil, discloses a process for dewaxing a hydrocarbon feedstock containing paraffins selected from the group of normal paraffins and slightly branched paraffins and sulfur and nitrogen compounds where, after conventionally hydrotreating the feedstock to remove sulfur and nitrogen, the hydrotreated feedstock is dewaxed by contacting the feedstock with a catalyst comprising $\beta$-zeolite having a silica/alumina ratio of at least 30:1.

In U.S. Pat. No. 4,740,292, to Mobil, there is disclosed a catalytic cracking process which comprises cracking a hydrocarbon feed in the absence of added hydrogen with a cracking catalyst comprising a $\beta$-zeolite component and a faujasite component comprising at least one crystalline aluminosilicate of the faujasite structure, the weight ratio of the faujasite component to the $\beta$-zeolite component being from 1:25 to 20:1.

Large pore $\beta$-zeolite has been employed in the synthesis of industrially important para-cumene by toluene isopropylation. See "Toluene Isopropylation over Zeolite $\beta$ and Metallosilicates of MFI Structure," P. A.

Parikh et al., APPLIED CATALYSIS, A, 1992, 90, p. 1.

It would be a valuable advance in the art if a method were available for the synthesis of methyl and ethyl tertiary butyl ether from tertiary butanol employing one step technology and a catalyst exhibiting product phase separation at operating temperatures of 140° C. or higher. The cosynthesis of isobutylene and diisobutylene using the crude feedstock reactants would make such a process even more attractive.

SUMMARY OF THE INVENTION

In accordance with certain of its aspects, the novel method of this invention for preparing methyl tert-butyl ether from tertiary butyl alcohol and methanol in one-step comprises reacting tertiary butyl alcohol and methanol in the presence of a catalyst comprising platinum/palladium-modified $\beta$-zeolite at an elevated temperature and moderate pressure, wherein the modified $\beta$-zeolite is optionally further treated with a halogen or Group IB metal. Ethyl t-butyl ether (ETBE) synthesis has also been confirmed.

DESCRIPTION OF THE INVENTION

Preparation of the product of this invention may be carried out typically by reacting tertiary butyl alcohol and methanol or ethanol in the presence of an etherification catalyst. The etherification is carried out in one-step and the catalyst preferably comprises a $\beta$-zeolite modified with one or more metals selected from Group VIII of the Periodic Table. In additional embodiments of the instant invention, the $\beta$-zeolite can be further modified with fluoride or copper.

The reaction can be represented by the following:

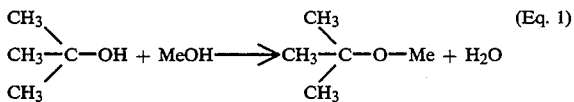       (Eq. 1)

Generally the methanol or ethanol and t-butanol coreactants may be mixed in any proportion in order to generate the desired methyl t-butyl ether (MTBE) or ethyl t-butyl ether (ETBE) but preferably the molar ratio of primary alcohol to t-butanol (tBA) in the feed mixture should be between 10:1 and 1:10, if the yield of desired MTBE or ETBE is to be maximized. In order to achieve maximum selectivity to MTBE or ETBE and optimum conversion per pass, an excess of primary alcohol in the liquid feed is desirable. The most preferred methanol or ethanol-to-tertiary butanol molar ratio is from 1:1 to 5:1.

In certain circumstances, it may be particularly desirable that the tBA conversion be high enough (e.g. 70% or greater), such that the crude product mix phase separates into an isobutylene-MTBE product-rich phase and a heavier aqueous ethanol phase. Optionally the MTBE-isobutylene phase will also contain diisobutylene. Preferably such a product phase separation would be achieved at as low an etherification temperature as possible, but it is particularly observed in the range 140°–200° C.

The synthesis of Eq. 1 can also be conducted where the t-butanol and methanol reactants are mixed with certain other components including water, ketones such as acetone (Ac₂O) and methyl ethyl ketone (MEK), peroxides and hydroperoxides such as di-t-butyl peroxide (DTBP) and allyl t-butyl peroxide (ATBP), and t-butyl hydroperoxide (TBHP), as well as esters such as t-butyl formate (TBF). Typically each of said classes of components makes up less than 10% of the total feed mixture.

The instant one-step process may also be applied to the preparation of other alkyl tertiary alkyl ethers. For example, said process may be applied to the reaction of a $C_1$–$C_6$ primary alcohol such as methanol, ethanol, n-propanol and n-hexanol with a $C_4$–$C_{10}$ tertiary alcohol such as, for example, tertiary butanol and tertiary amyl alcohol. Alternatively a mixture of alcohols, e.g., a mixture of $C_1$–$C_5$ alcohols, could be reacted to give a mixture of alkyl tert-alkyl ethers.

In addition, the catalyst of the instant invention could be employed as a trifunctional catalyst for the removal in the presence of hydrogen of diolefins and peroxides that are present in the $C_4$ or $C_5$ iso-olefin stream in the MTBE/TAME unit.

In the modified catalyst of the instant invention good results were realized using certain crystalline aluminosilicate zeolites as catalysts for the reaction represented in Eq. 1. Particularly effective were the isostructural group of $\beta$-zeolites.

$\beta$-zeolite was first synthesized at the Mobil Research and Development Laboratories. It exhibited improved thermal and acid stability over previously synthesized zeolites, Higgins et al., supra, p. 446.

The composition of $\beta$-zeolite is described in U.S. Pat. Nos. 3,308,069; 4,419,220; 4,518,485 and 4,740,292. In those references, $\beta$-zeolite is typically described as follows:

$\beta$-zeolite is a crystalline aluminosilicate having a pore size greater than 5 Angstroms. The composition of the zeolite, as described in U.S. Pat. No. 3,308,069, in its as synthesized form may be expressed as follows:

$$[XNa(1.0\pm0.1-X)TEA]AlO_2 \cdot YSiO_2 \cdot WH_2O$$

where X is less than 1, preferably less than 0.7; TEA represents the tetraethylammonium ion; Y is greater than 5 but less than 100; and W is up to about 60 (it has been found that the degree of hydration may be higher than originally determined, where W was defined as being up to 4), depending on the degree of hydration and the metal cation present. The TEA component is calculated by differences from the analyzed value of sodium and the theoretical cation to structural aluminum ratio of unity.

As discussed in the J. B. Higgins, et al. reference, supra, p. 446, the first clues to the crystal structure of $\beta$-zeolite were evidenced from chemical and physical property measurements. Ion-exchange isotherms of Na-$\beta$ at 25° C. indicated that cations as large as tetraethylammonium (TEA+) exchanged completely into the pore system. This behavior suggests that beta contains at least 12-membered rings opening into channels, because TEA+ is too large to exchange through 10-membered rings such as those in ZSM-5. The complete exchange of cations in beta indicated the presence of channels instead of cages, because it is not possible to remove all the cations from cage structures such as Na faujasite. Additional evidence was obtained from organic sorption data and density measurements. Cyclohexane sorption of 14.6–19.4 wt % and a measured density of 1.61 g/cm³ ruled out undimensional pore systems such as those in ZSM-12, ZSM-22, ZSM-23 and ZSM-48. Structural similarities among beta, mordenite and ZSM-12 were suspected because all three may be synthesized in Na+-TEA+systems from highly siliceous batch compositions. Further, β-zeolite is easily synthesized in the SiO2/Al2O3 range of 30-50. This lies between TEA+mordenite (typically 10-30) and ZSM-12 (typically, >60), suggesting the beta framework contains large fractions of both 4-and 5-membered rings.

In the Tsai and Wang reference, supra, part II, p. 209, stability enhancement is discussed. Two methods, silica deposition and steam pretreatment, have been developed to substantially improve β-zeolite stability.

At comparable conversion levels, the alpha value decreases from 0.23 for unmodified β-zeolite to 0.09 after mild steam pretreatment. Where β-zeolite is steam pretreated, apparently acid strength of the zeolite is enhanced and the yield of aromatics is increased, Ibid, p. 213.

In the fully base-exchanged form, β-zeolite has the composition:

$$[(X/n)M(1\pm 0.1-X)H]AlO_2 \cdot YSiO_2 \cdot WH_2O$$

where X, Y and W have the values listed above and n is the valence of the metal M. This form of the zeolite may be converted partly to the hydrogen form by calcination, e.g. at 200° C. to 900° C. or higher. The completely hydrogen form may be made by ammonium exchange followed by calcination in air or an inert atmosphere such as nitrogen, see U.S. Pat. 4,419,220.

β-zeolite is characterized by the following X-ray diffraction pattern:

d Values of Reflection in β-zeolite
11.40±0.2
7.40±0.2
6.70±0.2
4.25±0.1
3.97±0.1
3.00±0.1
2.20±0.1

The preferred forms of β-zeolite are the highly acidic, high silica forms, having silica-to-alumina mole ratio of at least 10:1, and preferably in the range of 10:1 to 50:1 in the as-synthesized form. A narrower range of 20:1 to 30:1 is most preferred. It has been found, in fact, that β-zeolite may be prepared with silica-to-alumina mole ratios above the 200:1 maximum specified in U.S. Pat. No. 3,308,069 and these forms of the zeolite may perform well in the process. Ratios of 50:1, or even higher, may be used where available.

Illustrative of suitable β-zeolites for the practice of this invention include Valfor C806β, Valfor CP815β and Valfor C861. Valfor ® is the registered trademark of the PQ corporation. Valfor ® C806β zeolite is β-zeolite powder in template cation form. It is a high silica shape selective zeolite which contains the organic template used in the crystallization step, having been isolated after filtration and washing of the synthesis product. C806βhas a SiO2/Al2O3 molar ratio of 23-26; the crystal size is 0.1-0.7 um; the surface area after calcination is about 700-750 m²/g; the cyclohexane adsorption capacity after calcination is 19-24g/100g; Na2O content is about 0.01-1.0% by weight anhydrous; and, the organic content is about 11-13% by weight, on a water-free basis.

Valfor ® C815β zeolite is a calcined β-zeolite powder in hydrogen, sodium form. It is similar to C806β except the product has been calcined to decompose the organic template. C815β is a high silica, shape selective aluminosilicate with a large pore diameter. C815β also has a SiO2/Al2O3 molar ratio of about 23-26; the crystal size, surface area, cyclohexane adsorption capacity and Na2O are all within the same ranges as given for C806β.

Valfor ® C861β is an extrudate made of 80% C815β powder and 20% alumina powder.

The metals useful for modifying the zeolite in the instant invention comprise those from Group VIII of the Periodic Table including, iron, ruthenium, cobalt, rhodium, nickel, palladium and platinum. Preferred metals are platinum and palladium. Especially good results were observed using a β-zeolite treated with ammonium hexafluorosilicate and subsequently treated with palladium.

Said zeolites are preferably impregnated with said specified metals as their salts, particularly their metal nitrate or chloride salts, in an aqueous, alcoholic, or ketonic media over a period of 1-24 hours, then the solids are filtered off, dried at elevated temperature, e.g. 120° C., for a period of time and calcined at 300°-800° C. for a further period, e.g. 530° C. for 5 hours followed by reduction in a stream of hydrogen at 100°-600° C.

The palladium-containing precursor compound to be dispersed into the β-zeolite is prepared by first dissolving or slurring the selected palladium salt, halide, etc., e.g., palladium(II) salt, with a suitable solvent system and subsequently impregnating the β-zeolite with the palladium-containing mixture. These solutions or slurries may be poured onto the zeolite, or the zeolite may be immersed in an excess of the liquid solution or slurries, with the excess being subsequently removed.

The palladium-containing precursor compound to be dispersed upon the zeolite may be impregnated on said zeolite in the form of a bivalent palladium-containing salt, such as, for example, palladium acetate, palladium propionate, palladium acetylactonate, palladium nitrate and the like. Alternatively, it can be added in the form of a palladium halide, such as palladium chloride. The examples demonstrate the use of tetraminepalladium(II) nitrate, Pd(NH3)4(NO3)2.

Where the β-zeolite is modified with platinum, it is preferably in the form of a nitrate or halide. Various possible platinum catalysts would include PtCl2, PtBr2, (PhCN)2PtCl2, (Ph3P)2PtCl2, Pt(acac)2 or tetraamineplatinum(II) nitrate, Pt(NH3)4(NO3)2.

Particularly effective in the subject synthesis of ETBE or MTBE are the palladium/platinum-modified β-zeolites further modified with a halogen compound or a Group IB compound, particularly copper and silver compounds.

Halogens which may be employed include fluoride, chloride, bromide and iodide compounds. Fluoride-containing compounds are preferred. Good results were observed using ammonium hexafluorosilicate.

The copper containing compound is added to the zeolite in the form of a salt of copper such as halide, sulfate, trifluoroacetate, nitrate, naphthalenate, hex-3-endioates or acetate. Copper salts which work include, but are not limited to copper(II) chloride, copper(II) bromide, copper(II) sulfate, cuprous chloride hydrate, copper(II) trifluoroacetate, copper(II) acetate, copper-(II) triflate, copper(II) fluorosulfonate, copper(I) chloride and copper(I) sulfate.

The amount of the various metals impregnated into the zeolite can vary. The amount of each individual metal, i.e., palladium, platinum, fluorine and copper can vary from 0.01 to 10.0%. Where palladium and platinum are deposited on β-zeolite the preferred weight percent is from 0.1% to 1.0%.

Example 1 demonstrates the preparation of the modified catalysts. Salts containing fluorine and palladium in anhydrous or hydrated forms were dissolved in water, alcohol, or acetone and the β-zeolites were added. The catalysts were then calcined by heating to 300° to 800° C. and optionally reduced in a stream of hydrogen at 100° to 600° C.

Said catalysts may be in the form of powders, pellets, granules, spheres, shapes and extrudates. The examples described herein demonstrate the advantages of using extrudates.

The reaction may be carried out in either a stirred, slurry reactor or in a fixed bed continuous flow reactor. The catalyst concentration should be sufficient to provide the desired catalytic effect.

Said catalysts may be formed in the presence of a binder, such as Group III or Group IV oxide. Group III or IV oxides used in conjunction with said palladium/-platinum-modified β-zeolite include oxides of aluminum, silicon, titanium, zirconium, hafnium, germanium, tin and lead, as well as combinations thereof. Alumina is preferred. Said binders may comprise 10% to 90% of the formed catalyst.

Etherification can generally be conducted at temperatures from 20° to 250° C.; the preferred range is 80° to 200° C. Good results are observed throughout this temperature range. The total operating pressure may be from 0 to 1000 psig, or higher. The preferred pressure range is 50 to 500 psig.

Typically, MTBE is generated continuously in up to ca. 40 wt % concentration or greater in the crude liquid product at total liquid hourly space velocities (LHSV) of up to 6 or higher and relatively mild conditions, where:

$$LHSV = \frac{\text{Volume Of Total Liquid Feed Run Through The Reactor Per Hour}}{\text{Volume Of Catalyst In Reactor}}$$

Conversions of t-butanol (tBA, wt %) are estimated in the following examples using the equation:

$$\frac{(\text{Mole \% of tBA in Feed} - \text{Mole \% of tBA in Product})}{\text{Mole \% of tBA in Feed}} \times 100$$

The examples which follow illustrate the one-step synthesis of MTBE from tBA and MeOH (Eq. 1) using palladium/platinum-modified β-zeolites particularly in the form of extrudates. Ethyl t-butyl ether (ETBE) synthesis has also been confirmed.

In particular, the accompanying examples illustrate:
1) The cosynthesis of MTBE, isobutylene, diisobutylene in Example 3 from t-butanol/methanol via etherification, dehydration and dimerization reactions using a palladium, fluoride-modified β-zeolite catalyst, prepared by the method of Example 1. Here the tBA conversion levels vary from 69% to 96% per pass over the operating temperature range 120°-180° C. Product phase separation into a lighter, diisobutylene, isobutylene, MTBE product phase and a heavier aqueous methanol phase is achieved at temperatures from 140° C. and above. A wide range of MTBE, isobutylene and diisobutylene selectivities have been demonstrated in this experiment.

2) In Examples 4–7, the cosynthesis of MTBE, isobutylene and diisobutylene from MeOH/tBuOH are illustrated using:
   a. A palladium, copper-modified β-zeolite.
   b. A platinum-modified β-zeolite.
   c. A palladium, fluoride-modified β-zeolite with 70% alumina binder.
3) In Example 8, ethyl t-butyl ether synthesis from ethanol and t-butanol is demonstrated using the palladium, fluoride-modified β-zeolite catalyst of Example 1.

EXAMPLE 1

This example illustrates the preparation of a palladium-modified β-zeolite.

To 110g of β-zeolite (090-92-1027-700, 50% β-zeolite, 50% alumina calcined at 530° C. for 3 hours) in 1/16" diameter extruded form was added a solution of 1.72g of ammonium hexafluorosilicate in 84 ml of distilled water. Impregnation of the β-zeolite was allowed to proceed over 1-2 hours, then the solids were filtered off, dried at 120° C., and calcined at 530° C. for 2 hours.

The fluorosilicate-treated zeolite was next mixed with a solution of 0.69g of tetraaminepalladium(II) nitrate, Pd(NH$_3$)$_4$(NO$_3$)$_2$, in 90 ml of distilled water, the solids recovered by filtration and then dried at 120° C. overnight, calcined at 530° C. for 5 hours, and finally reduced in a stream of hydrogen at 200° C.

The grey-colored extrudates (052-92-6887-021) were found by analysis to contain:
0.24% fluoride
0.2% palladium

EXAMPLE 2

This example illustrates the preparation of a platinum-modified β-zeolite.

To 176g of β-zeolite (090-92-1027-700, 50% β-zeolite, 50% alumina) in 1/16" diameter extruded form was added a solution of 1.75g of tetraamineplatinum(II) nitrate, Pt(NH$_3$)$_4$(NO$_3$)$_2$, in 120 ml of distilled water. Impregnation of the β-zeolite was allowed to proceed over 1-2 hours, then the solids were filtered off, dried at 120° C. for 2 hours, calcined at 530° C. for 3 hours and finally reduced at 400° C. in a stream of hydrogen for 4 hours.

The brown-black extrudates (052-92-6887-047) were found by analysis to contain:
0.22% platinum

EXAMPLE 3

This example illustrates the production of methyl t-butyl ether from t-butanol and methanol using the palladium-impregnated β-zeolite of Example 1.

Synthesis was conducted in a tubular reactor (½" i.d., 12" long) constructed of 316 stainless steel, operated upflow and mounted in a furnace, controllable to ±1.0° C. and fitted with pumps allowing flow control to <±1 cc/hr. The reactor was also fitted with a pressure regulating device and equipment for monitoring temperature, pressure and flow rate. The reactor was charged at the beginning of the experiment with 25 of palladium-treated β-zeolite, prepared by the procedure of Example 1, as 1/16" diameter extrudates. A screen of glass wool was placed at the top and bottom of the reactor to ensure the catalyst would remain in the middle portion. The catalyst bed was treated with a methanol/t-butanol (1.1:1 molar mix) upflow, at a rate of 50 cc/hr, while the reactor was held at 120° C., with a total pressure of 300 psi. Samples of crude product effluent were collected periodically on stream, in 316 ss bombs and analyzed by glc.

Typical analyses data for samples taken under these conditions are summarized in Table 1. Concentrations of MTBE, isobutylene, diisobutylene, methanol, t-butanol in the product effluent were also measured at a series of higher temperatures (140°–180° C.). These data are also included in Table 1.

For Sample #2, at 120° C.:
   tBA conversion = 69%
   MTBE selectivity = 73%
   Isobutylene selectivity = 20%
   Diisobutylene selectivity = 5%
For Sample #7, at 180° C.:
   tBA conversion = 96%
   MTBE selectivity = 12%
   Isobutylene selectivity = 71%
   Diisobutylene selectivity = 20% determined by glc, are summarized for each catalyst in the accompanying Tables 2 to 5.

The catalysts evaluated include:
a) A 1% F., 0.3% Pd on 50% β-zeolite, 50% alumina, reduced at 200° C. (Sample 052-92-6887-219, Example 4, Table 2).
b) A 0.2% Pd, 2% Cu on 50% β-zeolite, 50% alumina, reduced at 200° C. (Sample 052-92-6887-128, Example 5, Table 3).
c) A 0.2% Pt on 50% β-zeolite, 50% alumina, reduced at 400° C. and prepared by the procedures of Example 2 (Sample 052-92-6887-047, Example 6, Table 4).
d) A 1% F., 0.3% Pd on 30% β-zeolite, 70% alumina (Sample 052-92-6887-119, Example 7, Table 5).

All four modified β-zeolites give high yields of MTBE at the lower operating temperatures (e.g. 120° C.) and high yields of isobutylene at the higher temperatures (e.g. 160° C). Of note, for the platinum-modified

TABLE 1

| Ex. | Catalyst | MeOH/tBA Molar Ratio | Feed Rate (cc/hr) | Temp. (°C.) | Time On Stream (Days) | Sample | $H_2O$ | MeOH | $C_4H_8$ | tBA | MTBE | $C_8H_{16}$ |
|---|---|---|---|---|---|---|---|---|---|---|---|---|
| 3 | Ex. 1 | 1.1:1 | 50 | | | FS-1 | | 31.3 | | 68.2 | | |
| | | | | 120 | 1 | 1 | 11.6 | 18.4 | 7.1 | 21.0 | 41.5 | 3.6 |
| | | | | | | 2 | 11.7 | 18.6 | 7.2 | 21.0 | 41.2 | 3.6 |
| | | | | 140 | 2 | $3^b$ | $a$ | | | | | 15.9 |
| | | | | | | | 23.3 | 32.9 | 4.3 | 16.2 | 22.5 | 5.2 |
| | | | | | | 4 | 8.5 | 20.8 | 13.0 | 15.7 | 41.7 | 15.6 |
| | | | | | | | 20.5 | 32.8 | 4.8 | 25.5 | 25.5 | 5.3 |
| | | | | 160 | 3 | $5^c$ | 1.4 | 11.1 | 28.6 | 7.3 | 51.0 | 25.4 |
| | | | | | | | 25.1 | 50.0 | 1.7 | 10.9 | 11.4 | 1.6 |
| | | | | | | | 0.8 | 6.6 | 16.7 | 4.9 | 29.6 | 26.8 |
| | | | | | | | 25.8 | 47.9 | 2.3 | 11.6 | 11.5 | 1.8 |
| | | | | 180 | 4 | $7^b$ | 0.3 | 4.2 | 52.5 | 1.4 | 12.6 | 23.9 |
| | | | | | | | 28.9 | 57.0 | 3.7 | 4.8 | 4.6 | 0.6 |
| | | | | | | 8 | 1.3 | 6.0 | 56.4 | 2.6 | 13.9 | 21.4 |
| | | | | | | | 28.4 | 57.6 | 3.5 | 5.2 | 4.3 | 0.4 |

$^a$No analyses data
$^b$Relative phase sizes 1.89:1 (t:b)
$^c$Relative phase sizes 1.55:1 (t:b)

EXAMPLES 4–7

Using the equipment and following the procedures of Example 3, various platinum and palladium-impregnated β-zeolite catalysts were treated with a 1.1:1 molar mix of methanol and t-butanol at a series of temperatures from 120° to 160° C. Concentrations of MTBE, isobutylene, diisobutylene, methanol and t-butanol in the product effluents, under the specified condition, as β-zeolite of Example 6:
At 120° C.:
   tBA conversion = 72%
   MTBE selectivity = 68%
   Isobutylene selectivity = 19%
   Diisobutylene selectivity = 9%
At 160° C.:
   tBA conversion = 92%

TABLE 2

| Ex. | Catalyst | MeOH/tBA Molar Ratio | Feed Rate (cc/hr) | Temp. (°C.) | Time On Stream (Days) | Sample | $H_2O$ | MeOH | $C_4H_8$ | tBA | MTBE | $C_8H_{16}$ |
|---|---|---|---|---|---|---|---|---|---|---|---|---|
| 4 | 052-92-6887-219$^a$ | 1.1:1 | 50 | | | FS-1 | | 31.2 | | 68.3 | | |
| | | | | 120 | 1 | 1 | 10.8 | 18.5 | 7.1 | 19.6 | 41.3 | 4.7 |
| | | | | | | 2 | 11.9 | 18.7 | 7.1 | 19.6 | 40.0 | 4.9 |
| | | | | 140 | 2 | $3^b$ | 4.4 | 13.8 | 12.1 | 11.1 | 36.5 | 21.1 |
| | | | | | | | 21.5 | 36.4 | 3.3 | 15.7 | 20.7 | 4.0 |
| | | | | | | $4^c$ | 6.2 | 16.0 | 11.2 | 11.6 | 34.9 | 18.9 |
| | | | | | | | 21.0 | 36.3 | 3.2 | 15.6 | 20.4 | 4.0 |
| | | | | 160 | 3 | $5^d$ | 0.7 | 5.7 | 17.1 | 3.9 | 26.4 | 25.3 |
| | | | | | | | 26.3 | 52.2 | 1.4 | 9.0 | 8.9 | 1.9 |
| | | | | | | $6^b$ | 0.7 | 6.1 | 18.3 | 3.6 | 26.6 | 26.0 |

TABLE 2-continued

| Ex. | Catalyst | MeOH/tBA Molar Ratio | Feed Rate (cc/hr) | Temp. (°C.) | Time On Stream (Days) | Sample | PRODUCT COMPOSITION (WT %) | | | | | |
|---|---|---|---|---|---|---|---|---|---|---|---|---|
| | | | | | | | $H_2O$ | MeOH | $C_4H_8$ | tBA | MTBE | $C_8H_{16}$ |
| | | | | | | | 26.3 | 51.0 | 1.6 | 9.7 | 9.5 | 1.3 |

[a] 1% F, 0.3% Pd on 50% Beta/Alumina, reduced at 200° C.
[b] Relative phase sizes 1.45:1 (t:b)
[c] Relative phase sizes 1.64:1 (t:b)
[d] Relative phase sizes 1.60:1 (t:b)

TABLE 3

| Ex. | Catalyst | MeOH/tBA Molar Ratio | Feed Rate (cc/hr) | Temp. (°C.) | Time On Stream (Days) | Sample | PRODUCT COMPOSITION (WT %) | | | | | |
|---|---|---|---|---|---|---|---|---|---|---|---|---|
| | | | | | | | $H_2O$ | MeOH | $C_4H_8$ | tBA | MTBE | $C_8H_{16}$ |
| 5 | 052-92-6887-128[a] | 1.1:1 | 50 | | | FS-1 | | 31.4 | | 68.1 | | |
| | | | | 120 | 1 | 1 | 10.5 | 17.5 | 7.3 | 18.2 | 42.9 | 3.9 |
| | | | | | | 2 | 10.6 | 18.0 | 7.1 | 19.0 | 42.4 | 4.3 |
| | | | | 140 | 2 | 3 | 4.6 | 13.8 | 11.6 | 11.3 | 37.0 | 18.9 |
| | | | | | | | 21.1 | 36.3 | 3.1 | 15.6 | 20.4 | 4.5 |
| | | | | | | 4[b] | 5.0 | 14.4 | 11.5 | 11.6 | 36.5 | 17.4 |
| | | | | | | | 20.4 | 35.7 | 3.3 | 15.5 | 21.1 | 4.3 |
| | | | | 160 | 3 | 5[c] | 0.9 | 5.6 | 15.2 | 3.5 | 26.9 | 25.2 |
| | | | | | | | 26.6 | 53.0 | 1.2 | 9.1 | 8.7 | 1.3 |
| | | | | | | 6[c] | 0.9 | 5.9 | 15.3 | 3.6 | 26.8 | 26.1 |
| | | | | | | | 26.2 | 51.8 | 1.4 | 9.5 | 9.3 | 1.3 |

[a] 0.2% Pd, 2% Cu on 50% Beta/Alumina, reduced at 200° C.
[b] Relative phase sizes 1.69:1 (t:b)
[c] Relative phase sizes 1.49:1 (t:b)

TABLE 4

| Ex. | Catalyst | MeOH/tBA Molar Ratio | Feed Rate (cc/hr) | Temp. (°C.) | Time On Stream (Days) | Sample | PRODUCT COMPOSITION (WT %) | | | | | |
|---|---|---|---|---|---|---|---|---|---|---|---|---|
| | | | | | | | $H_2O$ | MeOH | $C_4H_8$ | tBA | MTBE | $C_8H_{16}$ |
| 6 | 052-92-6887-047[a] | 1.1:1 | 50 | | | FS-1 | 31.4 | | | 68.1 | | |
| | | | | 120 | 1 | 1 | 11.7 | 18.3 | 6.9 | 19.2 | 39.6 | 5.1 |
| | | | | | | 2 | 11.8 | 18.4 | 6.9 | 19.1 | 39.5 | 6.7 |
| | | | | 140 | 2 | 3[b] | 3.5 | 12.1 | 12.2 | 9.7 | 36.4 | 21.5 |
| | | | | | | | 24.5 | 37.2 | 2.7 | 15.8 | 16.5 | 3.6 |
| | | | | | | 4[c] | 3.9 | 12.5 | 12.2 | 10.0 | 36.4 | 21.0 |
| | | | | | | | 24.4 | 36.8 | 2.9 | 14.4 | 18.5 | 3.8 |
| | | | | 160 | 3 | 5[d] | 0.8 | 5.5 | 15.5 | 3.0 | 25.2 | 27.0 |
| | | | | | | | 30.7 | 50.3 | 1.3 | 8.3 | 7.8 | 1.3 |
| | | | | | | 6[c] | 1.6 | 7.2 | 17.0 | 3.1 | 24.5 | 24.0 |
| | | | | | | | 27.2 | 52.1 | 1.5 | 8.3 | 9.1 | 1.3 |

[a] 0.2% Pd on 50% Beta/Alumina, reduced at 400° C.
[b] Relative phase sizes 1.17 (t:b)
[c] Relative phase sizes 1.5 (t:b)
[d] Relative phase sizes 1.37 (t:b)

TABLE 5

| Ex. | Catalyst | MeOH/tBA Molar Ratio | Feed Rate (cc/hr) | Temp. (°C.) | Time On Stream (Days) | Sample | PRODUCT COMPOSITION (WT %) | | | | | |
|---|---|---|---|---|---|---|---|---|---|---|---|---|
| | | | | | | | $H_2O$ | MeOH | $C_4H_8$ | tBA | MTBE | $C_8H_{16}$ |
| 7 | 052-92-6887-119[a] | 1.1:1 | 50 | | | FS-1 | 0.2 | 31.4 | | 68.1 | | |
| | | | | 120 | 1 | 1 | 10.7 | 17.9 | 7.4 | 19.7 | 41.5 | 3.4 |
| | | | | | | 2 | 11.0 | 17.9 | 7.3 | 20.1 | 40.9 | 3.4 |
| | | | | 140 | 2 | 3 | 9.9 | 19.3 | 9.7 | 14.2 | 33.4 | 14.3 |
| | | | | | | | 22.9 | 30.2 | 4.4 | 15.4 | 22.6 | 5.8 |
| | | | | | | 4 | 9.2 | 19.5 | 9.7 | 14.2 | 33.7 | 13.9 |
| | | | | | | | 20.3 | 31.5 | 4.5 | 15.5 | 23.6 | 5.9 |
| | | | | 160 | 3 | 5 | 1.2 | 7.1 | 26.7 | 4.8 | 25.0 | 23.0 |
| | | | | | | | 26.1 | 48.7 | 2.8 | 10.3 | 10.4 | |
| | | | | | | 6 | 1.2 | 7.3 | 28.9 | 4.7 | 26.9 | 22.0 |

TABLE 5-continued

| Ex. | Catalyst | MeOH/tBA Molar Ratio | Feed Rate (cc/hr) | Temp. (°C.) | Time On Stream (Days) | Sample | PRODUCT COMPOSITION (WT %) | | | | | |
|---|---|---|---|---|---|---|---|---|---|---|---|---|
| | | | | | | | $H_2O$ | MeOH | $C_4H_8$ | tBA | MTBE | $C_8H_{16}$ |
| | | | | | | | 22.8 | 54.9 | 2.7 | 8.8 | 9.5 | 1.4 |

<sup>a</sup>0.3% Pd, 1% F on 30% Beta, 70% Alumina

EXAMPLE 8

Using the equipment and following the procedure of Example 3, the palladium, fluoride-modified β-zeolite of Example 1 was treated with a 1.1:1 molar mix of ethanol and t-butanol at a series of temperatures from 120° C. to 160° C. Concentrations of ethyl t-butyl ether (ETBE), isobutylene, diisobutylene, ethanol and t-butanol in the product effluents, under the specified conditions, as determined by glc, are summarized in the accompanying Table 6.

d Values of Reflections in β-zeolite
11.40±0.2
7.40±0.2
6.70±0.2
4.25±0.1
3.97±0.1
3.00±0.1
2.20±0.1.

7. The method of claim 1 wherein the Group VIII metals are selected from the group consisting of iron, ruthenium, osmium, cobalt, rhodium, iridium, nickel,

TABLE 6

| Ex. | Catalyst | MeOH/tBA Molar Ratio | Feed Rate (cc/hr) | Temp. (°C.) | Time On Stream (Days) | Sample | PRODUCT COMPOSITION (WT %) | | | | | |
|---|---|---|---|---|---|---|---|---|---|---|---|---|
| | | | | | | | $H_2O$ | EtOH | $C_4H_8$ | tBA | ETBE | $C_8H_{16}$ |
| 8 | Ex. 1 | 1.1:1 | 50 | | | FS-1 | • | 40.5 | | 59.1 | | |
| | | | | 120 | 1 | 1 | 8.5 | 28.9 | 9.6 | 20.3 | 32.1 | 10.4 |
| | | | | | | 2 | 7.8 | 26.9 | 9.2 | 19.0 | 31.2 | 10.4 |
| | | | | 140 | 2 | 3<sup>b</sup> | a | | | | | |
| | | | | | | | 11.3 | 35.9 | 8.6 | 12.4 | 17.5 | 24.7 |
| | | | | | | 4 | a | | | | | |
| | | | | | | | 11.1 | 35.2 | 8.9 | 11.9 | 18.1 | 24.8 |
| | | | | 160 | 3 | 5<sup>c</sup> | 2.0 | 18.9 | 15.9 | 5.1 | 15.4 | |
| | | | | | | | 21.1 | 54.8 | 4.3 | 10.7 | 7.1 | e |
| | | | | | | 6<sup>d</sup> | 3.0 | 19.3 | 16.5 | 5.1 | 15.8 | |
| | | | | | | | 19.2 | 53.9 | 5.5 | 10.7 | 8.7 | e |

<sup>a</sup>Insufficient quantity for analysis
<sup>b</sup>Relative phase sizes 0.2:1 (t:b)
<sup>c</sup>Relative phase sizes 0.86:1 (t:b)
<sup>d</sup>Relative phase sizes 0.80:1 (t:b)
<sup>e</sup>Analysis not available

What is claimed is:

1. A method for synthesizing alkyl tertiary-alkyl ether which comprises reacting a $C_1$–$C_6$ primary alcohol with a $C_4$–$C_{10}$ tertiary alcohol in the presence of a catalyst comprising a β-zeolite modified with one or more metals from Group VIII of the Periodic Table, optionally further modified with a compound selected from the group consisting of a halogen and a Group IB metal, and continuously contacting said $C_1$–$C_6$ primary alcohol with a $C_4$–$C_{10}$ tertiary alcohol in a molar amount from about 10:1 to 1:10 over said zeolite catalyst at a temperature of about 20° to 250° C. and a pressure of about atmospheric to 1000 psi to obtain the desired alkyl tertiary ether product wherein the Group VIII metal-modified β-zeolite is reduced in a stream of hydrogen in the temperature range of 100° to 600° C.

2. The method of claim 1 wherein the $C_1$–$C_6$ primary alcohol is methanol and the $C_4$–$C_{10}$ tertiary alcohol is t-butanol.

3. The method of claim 1 wherein the $C_1$–$C_6$ primary alcohol is ethanol and the $C_4$–$C_{10}$ tertiary alcohol is t-butanol.

4. The method of claim 1 wherein the β-zeolite has a silica:alumina molar ratio of at least 10:1.

5. The method of claim 1 wherein the β-zeolite has a silica:alumina ratio of 10:1 to 50:1.

6. The method of claim 1 wherein the β-zeolite is characterized by the following X-ray diffraction pattern:

palladium and platinum.

8. The method of claim 1 wherein the Group VIII metal is palladium.

9. The method of claim 1 wherein the Group VIII metal is platinum.

10. The method of claim 1 wherein the palladium is impregnated into the β-zeolite as tetraminepalladium-(II) nitrate.

11. The method of claim 1 wherein the platinum is impregnated into the β-zeolite as tetraamineplatinum-(II) nitrate.

12. The method of claim 1 wherein the Group VIII-modified β-zeolite is modified with a halogen selected from the group consisting of fluorine, chlorine, bromine and iodine.

13. The method of claim 1 wherein the halogen is fluorine added as ammonium hexafluorosilicate.

14. The method of claim 1 wherein the Group VIII-modified β-zeolite is further modified with a metal selected from Group IB of the Periodic Table.

15. The method of claim 14 wherein the Group IB metal is selected form the group consisting of copper or silver.

16. The method of claim 16 wherein the Group IB metal is copper.

17. The method of claim 1 wherein the concentrations of metals impregnated into said zeolite may vary from 0.01% to 10.0% for each metal.

18. The method of claim 1 wherein the β-zeolite catalyst is formed in the presence of a Group III oxide.

19. The method of claim 1 wherein the Group III oxide binder is alumina.

20. The method of claim 19 wherein the alumina comprises 10% to 90% of the formed catalyst.

21. The method of claim 1 wherein the operating temperature is in the range of about 140° C. to 200° C. and the product comprises a two-phase mix of an ETBE-isobutylene, and, optionally, diisobutylene product rich phase and a heavier aqueous ethanol-rich phase.

* * * * *

UNITED STATES PATENT AND TRADEMARK OFFICE
CERTIFICATE OF CORRECTION

PATENT NO. : 5,364,981
DATED : November 15, 1994
INVENTOR(S) : John Frederick Knifton
Pei-Shing Eugene Dai It is certified that error appears in the above-identified patent and that said Letters Patent is hereby corrected as shown below:

In Claim 21, col. 18, line 1, after "1" insert --wherein the primary alcohol is ethanol and the tertiary alcohol is t-butanol and--.

In Claim 21, col. 18, line 4, delete "ETBE" and substitute therefor --ethyl t-butyl ether (ETBE)--.

In Claim 21, col. 18, line 4, please delete "optionally, diisobutylene".

Signed and Sealed this

Twenty-fourth Day of January, 1995

Attest:

BRUCE LEHMAN

*Attesting Officer*  *Commissioner of Patents and Trademarks*